United States Patent [19]
Yamagishi et al.

[11] 4,199,515
[45] Apr. 22, 1980

[54] NOVEL LONOMYCIN DERIVATIVES

[75] Inventors: Michio Yamagishi, Tokorozawa; Kazutoshi Mizoue, Urawa; Taku Mizutani, Ageo; Hiroshi Hara, Kitamoto; Sadafumi Omura, Ageo; Haruo Seto, Ueno; Noboru Otake, Yokohama, all of Japan

[73] Assignee: Taisho Pharmaceutical Co., Ltd., Tokyo, Japan

[21] Appl. No.: 18,935

[22] Filed: Mar. 9, 1979

[30] Foreign Application Priority Data

Mar. 16, 1978 [JP] Japan .................................. 53-30187
Mar. 16, 1978 [JP] Japan .................................. 53-30188

[51] Int. Cl.$^2$ .................... C07D 309/22; A61K 31/35
[52] U.S. Cl. .............................. 260/345.7 R; 424/283
[58] Field of Search ........................... 260/345.7 R; 260/345.8 R

[56] References Cited

U.S. PATENT DOCUMENTS 4,141,907  2/1979  Nakatsukasa et al. ........ 260/345.7 R

OTHER PUBLICATIONS

Omura et al., J. Antibiotics, 29, 15 (1976).

Primary Examiner—Nicky Chan
Attorney, Agent, or Firm—George A. Loud

[57] ABSTRACT

Novel lonomycin derivatives, prepared by reacting lonomycin or its salt with an alkali or an alkali metal borohydride, show antibacterial, antiviral and antiprotozoal activity, and have decreased toxicity as compared with lonomycin.

3 Claims, No Drawings

NOVEL LONOMYCIN DERIVATIVES

BACKGROUND

Lonomycin, from which the novel compounds of this invention are prepared, is a polyether type antibiotic produced by *Streptomyces ribosidificus* TM-481 (ATCC No. 31051) described in J. of Antibiotics, 29, No. 1, 15-20(1976), and is also designated as "antibiotic TM-481". This antibiotic has activity to gram positive bacteria and to protozoa such as coccidium, and is represented by the formula

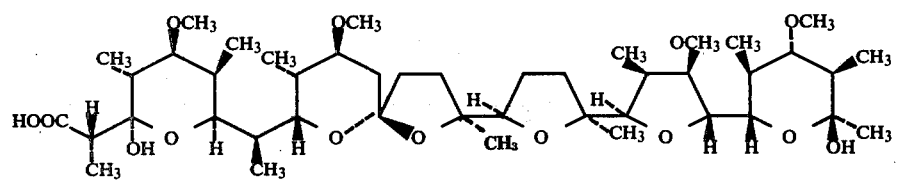

DESCRIPTION AND PREFERRED EMBODIMENTS

This invention relates to novel derivatives of lonomycin. More particularly, this invention is concerned with the novel compounds represented by the formula

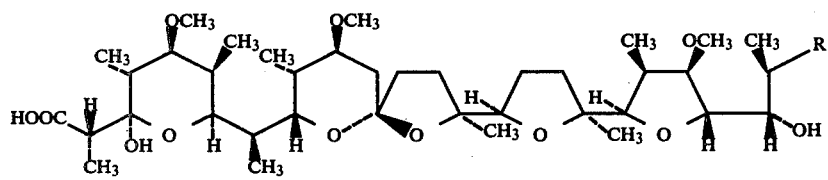

(I)

wherein R is 2-methyl-3-oxo-1-butenyl or 3-hydroxy-1-methoxy-2-methylbutyl, and pharmaceutically acceptable salts thereof.

An object of this invention is to provide the novel compounds which have antibacterial, antiviral and antiprotozoal activity and show lower toxicity than lonomycin.

In the formula(I), when R is 2-methyl-3-oxo-1-butenyl, the compound illustrated is designated as oxo-lonomycin, and when R is 3-hydroxy-1-methoxy-2-methylbutyl, the compound illustrated is designated as dihydro-lonomycin. The pharmaceutically acceptable salts of the compounds represented by the formula(I) include, but are not limited to, the corresponding alkali metal salts such as sodium and potassium salts, alkaline earth metal salts such as barium and magnesium salts, and unsubstituted and substituted ammonium salts.

Oxo-lonomycin of this invention may be prepared by the following method: In a water-miscible organic solvent such as acetone and methylethyl ketone, is dissolved lonomycin or its salt which may be prepared by treating lonomycin with an alkali metal base, alkaline earth metal base, or unsubstituted or substituted ammonium base in a known manner per se. As aqueous solution of an alkali such as sodium hydroxide or potassium hydroxide may be added to the resulting solution to adjust the pH to 11 or above. The mixture is allowed to stand at room temperature for 20-50 hours to give the salt of oxo-lonomycin as a precipitate. The precipitate may be collected by filtration, and purified by recrystallization.

The salt of oxo-lonomycin thus obtained may be converted to oxo-lonomycin in the form of the free acid by a conventional method. For example, the salt of oxo-lonomycin in dissolved in an organic solvent such as methanol and acetone, and added to an aqueous solution of a mineral acid such as hydrochloric acid. This solution is extracted with an organic solvent such as benzene or chloroform to give oxo-lonomycin in the form of the free acid. Oxo-lonomycin thus obtained may be also converted into its desired salt by treating with the alkali metal base, alkaline earth metal base, or unsubstituted or substituted ammonium base in a known manner.

Dihydro-lonomycin of this invention may be prepared by reduction of lonomycin or the above mentioned salt using an alkali metal borohydride such as sodium borohydride or potassium borohydride, in an inert solvent such as dioxane. The solution, (after adjusting the pH to about 4 with a mineral acid such as hydrochloric acid when using the salt of lonomycin as a starting material), is stirred at room temperature for 15-20 hours. After the precipitate formed is removed by filtration, the filtrate is diluted with water, and extracted with an organic solvent such as benzene. The extract is evaporated to give dihydro-lonomycin as a powder. This compound consists of two optical isomers, designated as dihydro-lonomycin I and dihydro-lonomycin II, showing the Rf values of 0.38 and 0.17, respectively, by thin layer chromatography on silica gel plate in a benzene-acetone (2:1) solvent system.

Further, the salt of dihydro-lonomycin may be prepared by treating dihydro-lonomycin with an alkali metal base, alkaline earth metal base, or unsubstituted or substituted ammonium base in a known manner, or prepared by the above mentioned method, but without the treatment of the salt of lonomycin with the mineral acid.

The optical isomers of dihydro-lonomycin or its salt may be separated by column chromatography. For example, the salt of dihydro-lonomycin is dissolved in benzene-acetone (3:1) and the resulting solution is applied to a silica gel column. For elution the same solvent as described above is used. The salt of dihydro-lonomycin I and the salt of dihydro-lonomycin II are eluted in the fractions between 1.2-1.9 times, and 2.25-3.1 times of the volume of the column used, respectively.

The compounds of this invention thus obtained have excellent activity to bacteria, especially, gram-positive bacteria, to virus, especially Newcastle disease virus, and to protozoa, especially the Eimeria and Toxoplasma species. Decreased toxicity is an important advantage provided by the compounds of this invention.

The acute toxicity of the compounds of this invention, administered intraperitoneally and intravenously to ddY male mice (20–22 g.) and expressed as $LD_{50}$, is shown in Table 1.

Table 1
(Acute toxicity of Ionomycin derivatives)

| Compounds | $LD_{50}$ (mg/kg) i.p. | i.v. |
|---|---|---|
| Sodium salt of dihydro-Ionomycin I | 11.3 | 6.0 |
| Sodium salt of dihydro-Ionomycin II | 15.2 | 10.8 |
| Sodium salt of oxo-Ionomycin | 117 | — |
| Sodium salt of Ionomycin | 8.3 | 4.9 |

The compounds of this invention can be used as an anticoccidial agent. For the control of coccidiosis in poultry, a nontoxic anticoccidial amount of the compound of this invention is administered to the birds, preferably orally on a daily basis. In case of the oral administration, the compounds of this invention may be supplied with a substance capable of being consumed by the birds, preferably the feed of the birds.

The rate of administration, which is effective against infection of coccidiosis, is generally in the range of from 100 to 700 ppm, preferably 250 to 500 ppm, by weight of unmedicated feed. The compound of this invention may be used optionally together with another anticoccidial agents.

The anticoccidial activity of the compounds of this invention is further illustrated by the tests involving *Eimeria tenella* in chickens.

For these studies, some groups of five 8-day-old chickens were fed a diet containing a compound of this invention, sodium salt of oxo-Ionomycin. The diet used has the following composition.
   47.0% corn
   10.0% barley flour
   10.0% defatted rice bran
   10.0% soy bean meal
   7.0% fish meal
   7.0% wheat bran
   3.0% lucerne meal
   3.0% sucrose
   3.0% $CaCO_3$
   0.5% NaCl
   0.5% Vitamin premix.

After having been on this ration for 48 hours, each chicken was inoculated with sporulated oocysts of *Eimeria tenella*. The other groups of five 8-day-old chickens were fed the diet which did not contain the test compound. One of these groups was also inoculated with *Eimeria tenella* after 48 hours and served as the infected control. The other of these groups was not inoculated with *Eimeria tenella* and served as a normal control. Medication was continued for 7 days after infective oocysts were administrated and then the results of treatment were evaluated.

The chickens were weighed, sacrificed and examined for evidence of coccidial lesions. Coccidial involvement was expressed on an arbitrary scale, increasing from minus (no evidence of coccidiosis) to four plus (maximum involvement for *Eimeria tenella*). The results of the test are shown in Table 2.

Table 2

| | Fecal score | Lesion score | | | | | Relative wt. gain % | Mortality |
|---|---|---|---|---|---|---|---|---|
| | | − | + | ++ | +++ | −+++ | | |
| Non-medicated group non infected | − | 5 | 0 | 0 | 0 | 0 | 100 | 0/5 |
| Non-medicated group infected | −+ | 0 | 0 | 0 | 1 | 4 | 40.1 | 3/5 |
| Medicated group 250 ppm | − | 1 | 1 | 2 | 1 | ) | 77.9 | 0/5 |
| Medicated group 500 ppm | − | 3 | 2 | 0 | 0 | ) | 91.8 | 0/5 |

Fecal score
−: normal
+: diarrhea
++: blood diarrhea
Lesion score
−: normal
+: insignificant
++: slight degree
+++: middle degree
++++: heavy degree The antitoxoplasma activity of the compounds of this invention was determined by the following method. The macrophage obtained intraperitoneally from mouse was cultured in 199 medium containing 20% heat inactivated calf serum, and was contacted with *Toxoplasma tachyzoites* (hereinafter referred to as "*T. tachyzoites*") for 1 hour at 37° C. Then, uninfected *T. tachyzoites* was washed out with phosphate buffer, pH 7.2. After the macrophage infected with *T. tachyzoites* was resuspended in the fresh medium, the test compound dissolved in ethanol was added to the macrophage suspension. The resulting mixture was incubated at 37° C. in 5% carbon dioxide in humidified air for 48 hours. After staining with trypan-blue, the survivals of *T. tachyzoites* in the macrophage were counted. The results are shown in Table 3.

Table 3
(Antioxoplasma activity of Ionomycin derivatives)

| | | Macrophage with *T. tachyzoites* | |
|---|---|---|---|
| | | 1–5 Tp/cell* | ≧6 Tp/cell** |
| Sodium salt of dihydro-Ionomycin I | 0.1 μg | 0 | 0 |
| Sodium salt of dihydro-Ionomycin II | 0.1 μg | 0.4 | 5.8 |
| Sodium salt of oxo-Ionomycin | 0.1 μg | 0 | 0 |

Table 3-continued

| (Antioxoplasma activity of Ionomycin derivatives) | | |
|---|---|---|
| | Macrophage with *T. tachyzoites* | |
| | 1–5 Tp/cell* | ≧6 Tp/cell** |
| None | 30.8 | 22.4 |

*Percentage of macrophage containing 1–5 T. tachyzoites per cell.
**Percentage of macrophage containing 6 or more T. tachyzoites per cell.

The compounds of this invention also show activity to Newcastle disease virus. This activity was determined by the red cell agglutination test. In this test, the cells were prepared from 8–10 day-old chick embryo by the usual method and cultured in Eagles' minimum essential medium to form a monolayer in a culture bottle. The results are shown in Table 4.

Table 4

| (Antiviral activity of Ionomycin derivatives) | |
|---|---|
| Compounds | Minimal inhibitory concentration |
| Sodium salt of dihydro-Ionomycin I | 3.1 μg/ml |
| Sodium salt of dihydro-Ionomycin II | 3.1 μg.ml |
| Sodium salt of oxo-Ionomycin | 0.8 μg/ml |

Furthermore, the compounds of this invention also exhibit inhibitory activity to bacteria. The minimal inhibitory concentration (MIC) at which the test compound inhibits various bacteria, determined by the agar dilution test, is summarised in Table 5. In this test, the aerobic bacteria used were streaked on heart infusion agar media containing various concentrations of the test compound. The anaerobic bacteria used were streaked on GAM media containing various concentrations of the test compound, and were incubated in an anaerobic incubator.

Table 5

| (Antibacterial activity of Ionomycin derivatives) | | | |
|---|---|---|---|
| | M.I.C. (μg/ml) | | |
| | Cpd. A | Cpd. B | Cpd. C |
| Anaerobic bacteria | | | |
| *Peptostreptococcus anaerobius* | 25 | 6.25 | 3.13 |
| *Peptostreptococcus produtus* | 12.5 | 3.13 | 3.13 |
| *Peptococcus magnus* | 1.56 | 1.56 | 1.56 |
| *Fusobacterium varium* | >100 | >100 | >100 |
| *Fusobacterium mortiferum* | >100 | >100 | >100 |
| *Bacteroides fragilis ss fragilis* | >100 | >100 | >100 |
| *Bacteroides fragilis ss distasonis* | >100 | >100 | >100 |
| *Bacteroides fragilis ss vulgatus* | >100 | >100 | >100 |
| *Propionibacterium acnes* | 50 | 25 | 12.5 |
| *Eubacterium aerofaciens* | 100 | 100 | 50 |
| *Eubacterium lentum* | 25 | 25 | 12.5 |
| *Eubacterium limosum* | 25 | 25 | 25 |
| *Clostridium perfringens* | >100 | 25 | 25 |
| *Clostridium sporogenes* | 25 | 25 | 25 |
| *Clostridium botulinum* | 15 | 12.5 | 12.5 |
| *Clostridium sordellii* | 12.5 | 12.5 | 6.25 |
| *Clostridium tetani* | 6.25 | 6.25 | 1.56 |
| Aerobic bacteria | | | |
| *Staphylococcus aureus* FDA 209P | 100 | 50 | 50 |
| *Staphylococcus aureus* Smith | >100 | >100 | >100 |
| *Bacillus subtilis* PCI 219 | 100 | 100 | 100 |

Cpd. A: Sodium of dihydro-Ionomycin I
Cpd. B: Sodium salt of dihydro-Ionomycin II
Cpd. C: Sodium salt of oxo-Ionomycin The following examples are provided to more fully illustrate the preparation of the compounds of this invention.

EXAMPLE 1

To a solution of 1.0 g of Ionomycin dissolved in 50 ml of dioxane, 0.3 g of sodium borohydride was added with stirring. An amount of water sufficient to dissolve the sodium borohydride was added dropwise. The solution was stirred overnight at room temperature. After the precipitate formed was removed by filtration, the filtrate was diluted with 50 ml of water, and extracted three times with 50 ml of benzene. The combined benzene extracts were washed twice with water, dried with sodium sulfate and evaporated to dryness in vacuo to give 0.8 g of dihydro-Ionomycin as a white powder.

Thin layer chromatography of the compound thus obtained on silica gel plate in benzene-acetone (2:1) shows the presence of two optical isomers with Rf values of 0.38 and 0.17.

EXAMPLE 2

To a solution of 2.0 g of sodium salt of Ionomycin dissolved in 100 ml of dioxane, 0.6 g of sodium borohydride was added. An amount of water sufficient to dissolve the sodium borohydride was added dropwise. The resulting solution was adjusted to pH 4 with 1 N hydrochloric acid, and then stirred overnight at room temperature. After the precipitate which formed, was removed by filtration, the filtrate was diluted with 100 ml of water, and then extracted three times with 100 ml of benzene. The combined benzene extracts were washed with water and evaporated to dryness to give 1.65 g of dihydro-Ionomycin as a white powder. Using the same chromatography as described in Example 1, the compound thus obtained shows Rf values of 0.38 and 0.17.

EXAMPLE 3

1.5 g of dihydro-Ionomycin, prepared as described in Example 2, was dissolved in 80 ml of methanol-water (3:1). This solution was adjusted to pH 10 by the addition of a 0.1 N aqueous solution of sodium hydroxide. The resulting solution was evaporated to dryness to give 1.5 g of sodium salt of dihydro-Ionomycin as a white powder.

EXAMPLE 4

1.0 g of sodium salt of dihydro-Ionomycin, prepared as described in Example 3, was dissolved in 5 ml of benzene-acetone (3:1) and applied on a silica gel column (100 ml) packed with the same solvent. For the elution from the column, the same solvent was used, and sodium salt of dihydro-Ionomycin I and sodium salt of dihydro-Ionomycin II were eluted in the fractions between 1.2 and 1.9 times and between 2.25 and 3.1 times of the volume of column, respectively. Each fraction was further purified by gel filtration on Sephadex LH-20 and crystallization from methanol to give white needles. Sodium salt of dihydro-Ionomycin I:yield, 0.35 g; melting point, 190°–191.5° C.; $[\alpha]_D^{25} = +23.6°$ (c=1, methanol); Elementary Analysis (%):Calcd. for $C_{44}H_{77}O_{14}Na$; C, 62.04, H, 8.93, O, 26.32, Na, 2.70, Found; C, 61.96, H, 9.17, O, 25.90, Na, 2.64; Rf value on thin layer chromatography, silica gel plate, benzene:acetone (2;1), 0.38. Sodium salt of dihydro-Ionomycin II:yield, 0.45 g; melting point, 160°–162° C.; $[\alpha]_D^{25} = +19.6°$ (c=1, methanol); Elemental Analysis(%):Calcd. for $C_{44}H_{77}O_{14}Na$; C, 62.04, H, 8.93, O, 26.32, Na, 2.70, Found; C, 61.18, H, 9.09, O, 25.85, Na, 2.67; Rf value on thin layer chromatography, silica gel plate, benzene:acetone (2:1), 0.17.

EXAMPLE 5

To a solution of 1.0 g of Ionomycin dissolved in 30 ml of acetone, 3 ml of a 3 N aqueous solution of sodium hydroxide was added. After standing for 30 hours at room temperature, the mixture was mixed with 2 ml of water and kept at 5° C. until the precipitate formed. The precipitate was collected by filtration and recyrstallized from aqueous methanol to give 760 mg of sodium salt of oxo-Ionomycin as white needles. Melting point, 199°–200° C.; $[\alpha]_D^{25} = +28.8°$ (c=1, methanol); Elementary Analysis(%): Calcd. for $C_{43}H_{71}O_{13}Na$; C, 63.06, H, 8.74, O, 25.40, Na, 2.81, Found: C, 62.95, H, 8.72, O, 25.18, Na, 2.90; $UV_{max}$ 231 m$\mu$ ($E_{1cm}^{1\%}$ 170, MeOH).

EXAMPLE 6

To a solution of 1.4 g of sodium salt of Ionomycin dissolved in 50 ml of acetone, 20 ml of a 1 N aqueous solution of sodium hydroxide was added with stirring. After a while, the mixture separated into two layers. The lower layer was removed, and the upper layer was allowed to stand for two days at room temperature and for another one day at 5° C. The precipitate formed was collected by filtration, and recrystallized from an aqueous methanol to give 950 mg of sodium salt of oxo-Ionomycin as white needles.

What we claim is:

1. Novel Ionomycin derivatives represented by the general formula

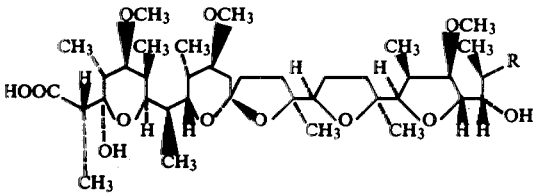

wherein R is 2-methyl-3-oxo-1-butenyl or 3-hydroxy-1-methoxy-2-methylbutyl, and pharmaceutically acceptable salts thereof.

2. A compound according to claim 1 wherein R is 2-methyl-3-oxo-1-butenyl, and its pharmaceutically acceptable salts.

3. A compound according to claim 1 wherein R is 3-hydroxy-1-methoxy-2-methylbutyl, and its pharmaceutically acceptable salts.

* * * * *